United States Patent
Dolle et al.

(10) Patent No.: US 6,995,261 B2
(45) Date of Patent: Feb. 7, 2006

(54) 4-PYRIDAZINECARBOXAMIDES AND ESTERS AS INTERLEUKIN-1β CONVERTING ENZYME INHIBITORS

(75) Inventors: Roland E. Dolle, King of Prussia, PA (US); Denton W. Hoyer, Exton, PA (US); Tina Morgan Ross, Audubon, PA (US); James M. Rinker, Reading, PA (US); Stanley J. Schmidt, Chester Springs, PA (US); Mark A. Ator, Paoli, PA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/668,475

(22) Filed: Sep. 22, 2003

(65) Prior Publication Data

US 2004/0110725 A1    Jun. 10, 2004

Related U.S. Application Data

(60) Division of application No. 08/625,680, filed on Apr. 3, 1996, now Pat. No. 6,624,166, which is a continuation of application No. 08/452,767, filed on May 30, 1995, now abandoned, which is a continuation of application No. 08/073,914, filed on Jun. 8, 1993, now abandoned.

(51) Int. Cl.
C07D 237/24    (2006.01)
C07D 401/04    (2006.01)
C07F 9/38      (2006.01)
A61K 31/501    (2006.01)
A61P 19/02     (2006.01)

(52) U.S. Cl. ............... 544/238; 544/114; 544/224; 544/232; 544/239; 544/241; 514/85; 514/236.5; 514/247; 514/252.01; 514/252.03; 514/252.04; 514/252.05

(58) Field of Classification Search ............... 514/247, 514/252.01, 252.03, 252.04, 252, 85, 236.5; 544/224, 232, 238, 239, 114, 241
See application file for complete search history.

(56) References Cited

U.S. PATENT DOCUMENTS

| | | | |
|---|---|---|---|
| 4,215,109 A | 7/1980 | Ruhenstroth-Bauer et al. | 424/177 |
| 4,590,194 A * | 5/1986 | Lesher et al. | 514/247 |
| 4,710,499 A | 12/1987 | Wermuth et al. | 514/247 |
| 5,055,451 A | 10/1991 | Krantz et al. | 514/19 |
| 5,081,145 A | 1/1992 | Guindon et al. | 514/419 |
| 5,418,233 A * | 5/1995 | Linz et al. | 514/247 |
| 6,121,266 A | 9/2000 | Dolle et al. | 514/252.03 |

FOREIGN PATENT DOCUMENTS

| | | |
|---|---|---|
| EP | 0 193 249 | 9/1986 |
| EP | 0 519 748 A2 | 12/1992 |
| EP | 0 537 696 A1 | 4/1993 |
| WO | WO 91/15577 | 10/1991 |

OTHER PUBLICATIONS

Wermuth et al, J.Med.Chem., 32, 1989, 528-537.*
Heinisch, Gottfried: Lassnigg, Doris Archiv der Pharmazie (Weinheim, Germany), 320(12), 1222-6 (German) 1987.*
G Ku, P Ford, SA Raybuck, MW Harding, JCR Randles, 65th Annual Meeting, American College of Rheumatology, Nov., 2001, Abstract #1134.*
Dornow et al., "Synthesen von Pyrazolo[3,4-c]pyridazinen", Chem. Ber., 97, 3349-3353 (1964).
Wermuth et al., "3-Aminopyridazine Derivatives with Atypical Antidepressant, Serotonergic, and Dopaminergic Activities", *J. Med. Chem.*, 32, 528-537 (1989).

* cited by examiner

Primary Examiner—Thomas C. McKenzie
(74) Attorney, Agent, or Firm—Fish & Neave IP Group Ropes & Gray LLP; James F. Haley, Jr.; Tae Bum Shin

(57) ABSTRACT

Disclosed are compounds of the formula (I) and pharmaceutically acceptable salts thereof:

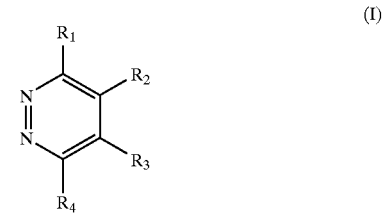

(I)

wherein
$R_1$ is a halogen, or an oxygen linked leaving group including an aromatic ether, an alkyl sulfonate, an aryl sulfonate, an alkyl phosphonate, an aryl phosphonate, an alkyl phosphate or aryl phosphate;
$R_2$ is $COOR_5$, $C(=O)NH(CHR_5)_m$—$COOR_5$, $NH(CHR_5)_m CON(R_5)R_6$, $C(=O)N(R_5)R_6$ or $NH(CHR_5)_m OH$;
$R_3$ is H or alkyl;
$R_4$ is H, substituted or unsubstituted aryl, heteroaryl or alkyl;
$R_5$ and $R_6$ are independently H, lower alkyl, aryl, hydroxy alkyl, amino alkyl, heteroaryl, lower alkylene-aryl, lower alkylene-heteroaryl or lower cycloalkyl; and m=0–6; pharmaceutical compositions containing the compounds; and a method for inhibiting interleukin-1β protease activity in a mammal utilizing the compounds and compositions.

9 Claims, No Drawings

4-PYRIDAZINECARBOXAMIDES AND ESTERS AS INTERLEUKIN-1β CONVERTING ENZYME INHIBITORS

CROSS-REFERENCE TO RELATED APPLICATIONS

This application is a divisional of U.S. patent application Ser. No. 08/625,680, filed Apr. 3, 1996, now U.S. Pat. No. 6,624,166, which is a continuation of U.S. patent application Ser. No. 08/452,767, filed May 30, 1995, now abandoned, which is a continuation of U.S. patent application Ser. No. 08/073,914, filed Jun. 8, 1993, now abandoned.

BACKGROUND OF THE INVENTION

1. Field of the Invention

This invention relates to a series of novel pyridazine analogs which exhibit selective inhibition of interleukin-1β converting enzyme, to compositions containing the novel pyridazine analogs and methods for therapeutic utility. More particularly, the interleukin-1β converting enzyme inhibitors described in this invention comprise novel pyridazine analogs which possess particular utility in the treatment of inflammatory, immune-based diseases and cancer.

2. Reported Developments

Interleukin-1β protease (also known as interleukin-1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A. *Proc. Nat. Acad. Sci.*, 1989, 86, 5227–5231 and Black, R. A.; Kronheim, S. R.; Sleath, P. R. *FEBS Let.*, 1989, 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, and acute and chronic myelogenous leukemia (Dinarello, C. A.; Wolff, S. M., *New Engl. J. Med.*, 1993, 328, 106). The naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., *Nature*, 1990, 343, 336–340; Eisenberg, S. P.; Evans, R. J.; Arend, W. P.; Verderber, E.; Brewer, M. T.; Hannum, C. H.; Thompson, R. C., *Nature* 1990, 343, 341–346; Ohlsson, K.; Bjork, P.; Bergenfeldt, M.; Hageman, R.; Thompson, R. C., *Nature*, 1990, 348, 550–552; and Wakabayashi, G., *FASEB*, 1991, 338–343). The specific role of IL-1β in inflammation and immunomodulation is supported by the recent observation that the cowpox virus employs an inhibitor of ICE to suppress the inflammatory response of its host (Ray, C. A. et al, *Cell*, 1992, 69, 597–604).

The present invention also relates to the modulation of processing of IL-1β for the treatment of rheumatoid arthritis. Levels of IL-1β are known to be elevated in the synovial fluid of patients with the disease. Additionally, IL-1β stimulates the synthesis of enzymes believed to be involved in inflammation, such as collagenase and PLA$_2$, and produces joint destruction which is very similar to rheumatoid arthritis following intra-articular injection in animals.

ICE is believed to be a cysteine protease (Thornbury, N. A. et al, *Nature*, 1992, 356–768). Peptidyl methyl ketone analogs constitute a well-known class of compounds having cysteine protease inhibitory activity. (D. Rich in Chapter 4 of "Proteinase Inhibitors", Barrett, A. J. and Salvensen, G., eds., Elsevier, 1986). However, there has never been a reported example of a non-peptide heterocyclic inhibitor of a cysteine protease. Hence, the inhibitory activity displayed by the pyridazine analogs described herein against ICE is unique.

An effective therapy has yet to be developed for the treatment of IL-1β mediated inflammatory diseases. Consequently, there is a need for therapeutic agents effective in the treatment and prevention of these diseases.

SUMMARY OF THE INVENTION

In accordance with the present invention, novel non-peptidic pyridazines are provided having the formula (I) and a pharmaceutically acceptable salt thereof

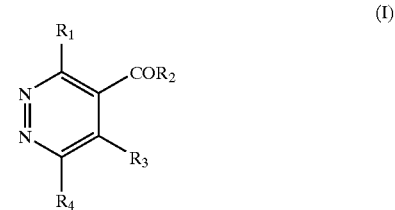

(I)

wherein
R$_1$ is a halogen, or an oxygen linked leaving group including an aromatic ether, an aromatic ester, an alkyl sulfonate, an aryl sulfonate, an alkyl phosphonate, an aryl phosphonate, an alkyl phosphate or aryl phosphate;
R$_2$ is OR$_5$, NH(CHR$_5$)$_m$—COOR$_5$, NH(CHR$_5$)$_m$CON(R$_5$)R$_6$, N(R$_5$)R$_6$ or NH(CHR$_5$)$_n$OH;
R$_3$ is H or alkyl;
R$_4$ is H, substituted or unsubstituted aryl, heteroaryl or alkyl;
R$_5$ and R$_6$ are independently H, lower alkyl, aryl, heteroaryl, aralkyl, heteroaralkyl or lower cycloalkyl;
m=1–6; and
n=2–6.

As used herein, the term pharmaceutically acceptable salts includes the acid and base addition salts.

The term acid addition salts refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

"Alkyl" is defined as a saturated or unsaturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" is defined as an alkyl group as above, having 1 to 4 carbon atoms. Suitable lower alkyl groups are methyl, ethyl, n-propyl, isopropyl, butyl, tert-butyl, n-pentyl, neopentyl, n-hexyl, and n-heptyl.

"Lower cycloalkyl" is defined as a carbocyclic ring of 3–8 carbon atoms including cyclopropyl, cyclobutyl, cyclopentyl and cyclohexyl.

"Aryl" is defined as phenyl, naphthyl and substituted phenyl.

"Substituted phenyl" is defined as a phenyl group in which one or more of the hydrogens has been replaced by the same or different substituents including halo, lower alkyl, nitro, amino, acylamino, hydroxyl, lower alkoxy, aryl, heteroaryl, alkyl sulfonyl, arylsulfonamido, trifluoromethyl, morpholinoethoxy and morpholino-sulfonyl, and carbobenzoxy-methyl sulfamoyl.

"Halogen" is defined as chloride, fluoride, bromide or iodide.

"Heteroaryl" is defined as pyridyl, thienyl, furyl, thiazolyl, imidazolyl, pyrazolyl, triazinyl, quinolyl, and isoquinolyl.

"Substituted heteroaryl" means a heteroaryl group in which one or more of the hydrogens has been replaced by the the same or different substituents including halo, lower alkyl, nitro, amino, acylamino, hydroxyl, lower alkoxy, aryl, heteroaryl, lower alkoxy, alkylsulfonyl, trifluoromethyl, morpholinoethoxy, morpholino-sulfonyl, carbobenzoxy-methylsulfamoyl.

"Aralkyl" is defined as an alkyl group susbstituted by an aryl ring. For example, benzyl, phenethyl and 4-chlorobenzyl.

The present invention concerns a method for inhibiting ICE in a mammal by administering a therapeutically effective amount of a compound of the Formula (I) or a pharmaceutical composition containing a compound of the Formula (I) in a pharmaceutically acceptable carrier. The method of inhibition is directed for the treatment of IL-1β mediated, disease states or disorders which include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based diseass, such as hypersensitivity; auto-immune diseases, such as multiple sclerosis; bone diseases; and certain tumors.

The pharmaceutical composition of the present invention comprises an active ingredient of the compound of formula (I) in admixture with a pharmaceutically acceptable, non-toxic carrier. Such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

When administered orally (or rectally) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, syrup, methylcellulose, polyoxyethylene sorbitan monolaurate, methyl hydroxybenzoate, propyl hydroxybenzoate, talc, and magnesium stearate.

The compositions may be prepared by any of the methods well-known in the pharmaceutical art, for example as described in *Remington's Pharmaceutical Sciences,* 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition acylcarnitines (*Am. J. Physiol.* 251:3332 (1986). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt.2, B. H. Vickery and J. S. Nester, Eds., MTP Press, Lancaster, UK, 1987).

In general, for the uses as described in the present invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day. This administration may be accomplished by a single administration, by distribution over several applications or by slow release in order to achieve the most effective results. When administered as a single dose, administration will most preferably be in the range of from about 0.1 to 10 mg/kg of body weight.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

DETAILED DESCRIPTION OF THE INVENTION

Compounds of the present invention are prepared according to Schemes I, II and III.

ferred agent) at reflux temperature (80° C.) for 4 hours. The halogenating agent may be used neat or with inert solvent such as dioxane or toluene. The addition of a catalytic amount of DMF accelerates the reaction. Other suitable halogenating agents include phenylphosphinic dichloride and phorphorus trichloride.

The corresponding 3-bromopyridazines are prepared similarly by heating (5) with phosphorous oxybromide or phosphorus tribromide. The dichlorides (6) are isolated from the reaction mixture by removing excess halogenating agent and solvent in vacuo and dissolving the residue in hot acetonitrile or other polar inert solvent. The reaction of the dichlorides (6) in acetonitrile with alcohols or amines yield the desired esters or amides (7).

Referring to Scheme II, intermediate ketomalonate addition products (2) can be prepared by deprotonatoin of the acetophenones (1) with lithium diisopropylamine (LDA)

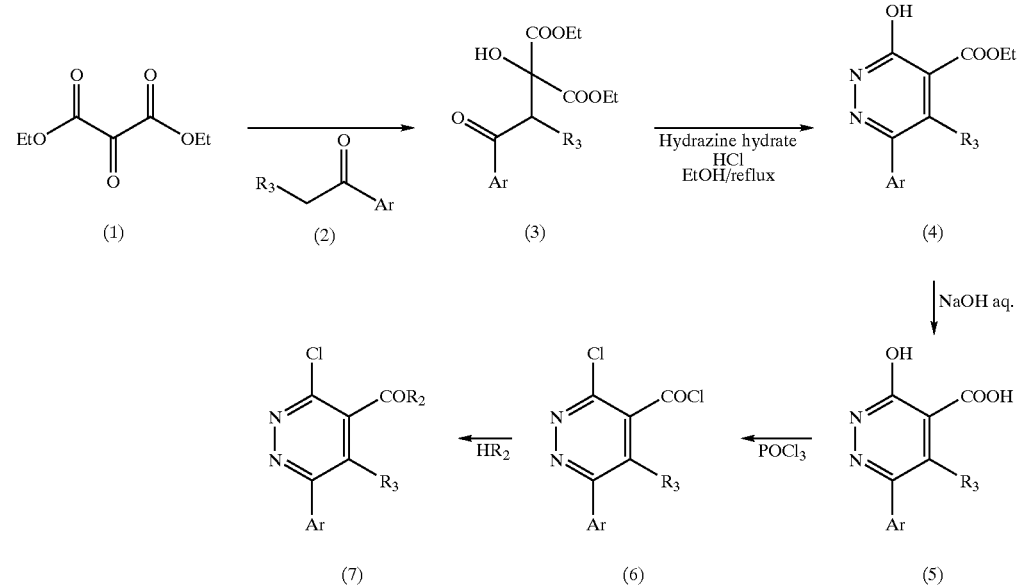

wherein $R_2$ and $R_3$ are defined previously.

Referring to Scheme I, the condensation of a-keto esters with aryl ketones to provide 6-aryl-3-hydroxypyridazines has been previously described [Druey, J. and von Schmidt, P. (1954) Helv. Chim. Acta., Vol. 37, 134]. Diethyl ketomalonate (1) and the aryl ketone (2) are heated together neat to approximately 120° C. for 15 hours to provide the condensation product (3). The keto-diester (3) is then treated with hydrazine in ethanol at reflux to form the 6-aryl-3-hydroxy-pyridazine (4), as crystalline solids. Saponification with aqueous alkali followed by neutralization provides the 3-hydroxy-carboxy-6-aryl-pyridazines (5). The conversion of 3-hydroxy-4-carboxy-6-aryl-pyridazines to their dichlorides (6) has been previously described in U.S. Pat. No. 4,590,194 and is performed by heating the pyridazines (5) with a halogenating agent (phosphorus oxychloride being the prefollowed by the addition of ketomatonate. This procedure was generally used for electron-rich aryl methyl ketones.

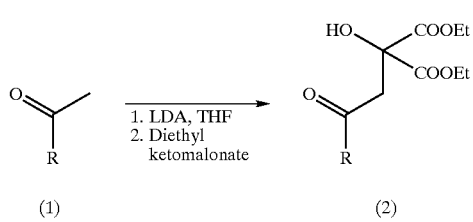

wherein R is phenyl, substituted aryl or heteroaryl.

Scheme III

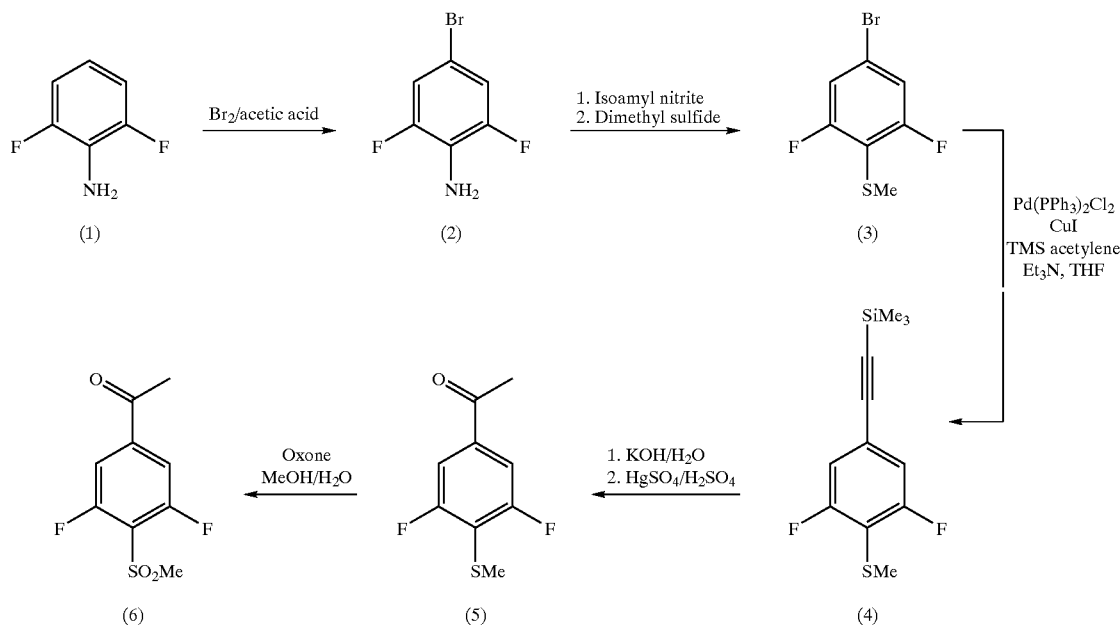

Referring to Scheme III, the intermediate 3,5-difluoro-4-(methylsulfonyl)-acetophenone (6) was prepared from commercially available 2,6-difluoroaniline. Bromination of the aniline (1) in acetic acid followed by diazotization and treatment of the diazonium salt with dimethylsulfide provides the thiomethyl derivative (3). Palladium catalyzed coupling reaction of (3) with trimethylsilyacetylene yield arylacetylene (4).

Alkaline hydrolysis of the silyl group followed by mercuration and acidic solvolysis affords ketone (5). Oxidation of the ketone with Oxone provides the desired 3,5-difluoro-4-(methylsulfonyl)-acetophenone (6).

The following examples further illustrate the invention and are not to be construed as limiting of the specification and claims in any way.

EXAMPLE 1

3-Chloro-4-carboxamido-6-(4-pyridyl)pyridazine

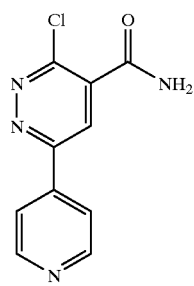

Diethyl ketomalonate (17.4 g, 0.1 mol) was heated with 4-acetylpyridine (12.1 g, 0.1 mol) at 120° C. for 15 h under nitrogen to provide diethyl 2-hydroxy-2-(4-pyridyl)cabonyl-methyl-malonate as a crystalline solid. The diester was refluxed in ethanol with a slight excess of hydrazine hydrate hydrochloride for 15 h to provide 3-hydroxy-6-(4-pyridyl)- 4-carbethoxy-pyridazine (4, Scheme 1). The above ester was recrystallized from ethanol, hydrolyzed with aqueous sodium hydroxide followed by careful neutralization with hydrochloric acid to afford 3-hydroxy-6-(4-pyridyl)-pyridazine-4-carboxylic acid (5, Scheme 1). The acid was dissolved in phosphorous oxychloride containing a catalytic amount of DMF and the mixture was allowed to react at 80° C. for 4 h to provide 3-chloro-4-chlorocarbonyl-6-(4-pyridyl)pyridazine (6, Scheme 1) as a dark oil. the above dichloride was treated with gaseous ammonia in acetonitrile to afford the title compound as a tan solid. The above dichloride was treated with excess gaseous ammonia to afford the title compound as a tan solid: $^1$H NMR (DMSO-d6) δ 8.80 (d, J=6 Hz, 2H), 8.59 (s, 1H), 8.20 (s, 1H), 8.17 (d, 6 Hz, 1H).

Utilizing appropriate starting materials and respects, and following the procedures described in the Schemes and Example 1, the following compounds were prepared.

EXAMPLE 2

3-Chloro-4-carboethoxy-6-(4-pyridyl)pyridazine

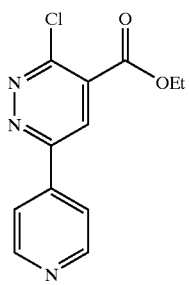

The title compound was prepared by treating pyridazine dichloride with anhydrous ethanol and a slight excess of triethylamine. The title compound was purified via silica gel chromatography (20% ethyl acetate/hexane). Anal. Calcd. for $C_{12}H_{10}ClN_3O_2$: C, 54.66; H, 3.82; N, 15.94. Found: C, 54.07; H, 3.80; N, 15.83.

EXAMPLE 3

3-Chloro-4-carboxamido-6-(3-pyridyl)pyridazine

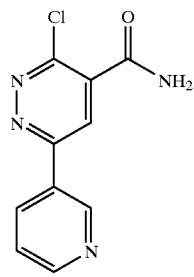

The title compound was prepared from 3-acetylpyridine. Anal. Calcd. for $C_{10}H_7ClN_4O_2$: C, 51.18; H, 3.09; N, 23.88. Found: C, 51.11; H, 3.09; N, 23.98.

EXAMPLE 4

3-Chloro-4-carboxamido-6-(4-bromophenyl)pyridazine

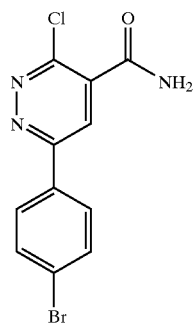

The title compound was prepared from 4-bromoacetophenone. Anal. Calcd. for $C_{11}H_7ClN_3O$: C, 42.27; H, 2.26; N, 14.44. Found: C, 42.24; H, 2.19; N, 13.34.

EXAMPLE 5

3-Chloro-4-carboxamido-6-(4-trifluoromethylphenyl)pyridazine

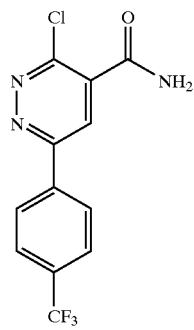

The title compound was prepared from 4-trifluoromethylacetophenone. Anal. Calcd. for $C_{12}H_7ClF_3N_3O$: C, 47.78; H, 2.34; N, 13.92. Found: C, 48.13; H, 2.14; N, 13.88.

EXAMPLE 6

3-Chloro-4-carboxamido-6-(3,5-dichlorophenyl)pyridazine

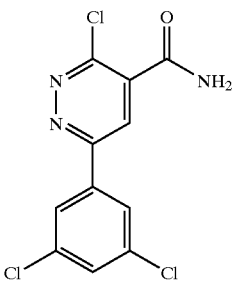

The title compound was prepared from 3,5-dichloroacetophenone. DCI-MS m/z 301.

EXAMPLE 7

3-Chloro-4-carboxamido-6-(2-naphthyl)pyridazine

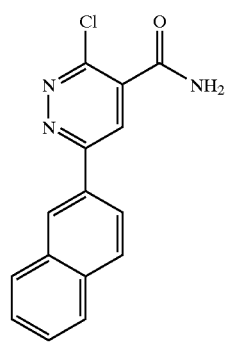

The title compound was prepared from 2-acetonaphthone. DCI-MS m/z 283 (M$^+$).

EXAMPLE 8

3-Chloro-4-carboxamido-6-(4-nitrophenyl)pyridazine

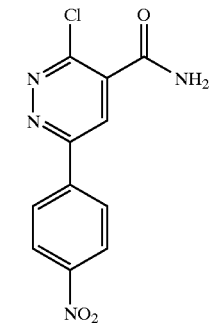

The title compound was prepared from 4-nitroacetophenone. FAB-MS m/z,279 (M+H+)

EXAMPLE 9

3-Chloro-4-carboxamido-6-(3-chloro-4-cyanophenyl)pyridazine

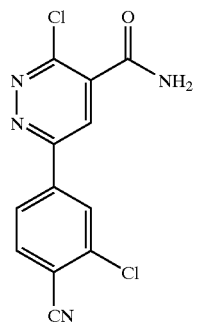

The title compound was prepared from 3-chloro-4-cyanoacetophenone. DCI-MS m/z 292.

EXAMPLE 10

3-Chloro-4-carboxamido-6-(2-pyrazyl)pyridazine

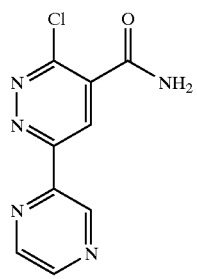

The title compound was prepared from 2-acetylpyrazine. DCI-MS m/z 236 (M+H).

EXAMPLE 11

3-Chloro-4-carboxamido-5-methyl-6-(4-chlorophenyl)pyridazine

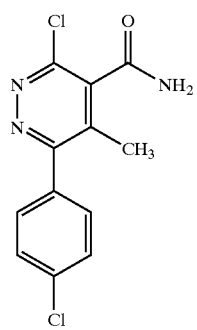

The title compound was prepared from 4-chloropropiophenone. DCI-MS m/z 282 (m+H+). $^1$H NMR (MeOD) δ 7.33 (s, 4H), 2.12 (s, 3H). Anal. Calcd. for $C_{12}H_9Cl_2N_3O$: C, 51.09; H, 3.22; N, 14.89. Found: C, 50.98; H, 3.34; N, 14.48.

EXAMPLE 12

3-Chloro-4-(2,4-dichlorobenzylaminocarbonyl)-6-(4-pyridyl)pyridazine

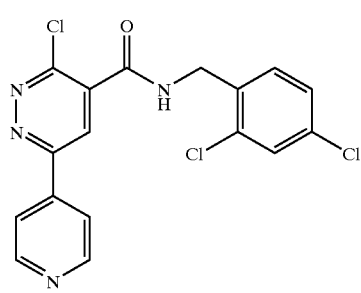

The title compound was prepared by treating the dichloride (6) with 2,4-dichlorobenzylamine according to Scheme I. DCI-MS m/z 392 (m+H+). $^1$H NMR (CDCl$_3$) δ 8.83 (d, J=6 Hz, 2H), 8.33 (a, 1H), 8.00 (d, J=6 Hz, 2H), 7.5 (m, 2H), 7.3 (m, 3H), 4.76 (d, J=6 Hz, 2H).

EXAMPLE 13

3-Chloro-4-[(C-ethoxy)glycyl]carbonyl)-6-(4-pyridyl)pyridazine

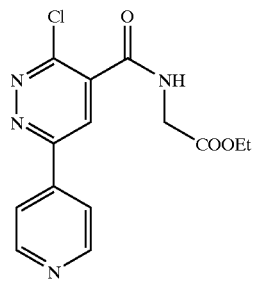

The title compound was prepared by treating the dichloride (6) with glycyl-ethyl ester according to Scheme I. DCI-MS m/z 320 (M+H). $^1$H NMR (DMSO-d$_6$) δ 8.80 (d, J=6 Hz, 2H), 8.52 (s, 1H), 8.16 (d, J=6 Hz, 2H), 4.13 (m, 4H), 1.22 (t, J=7.1 Hz, m, 3H).

EXAMPLE 14

3-Chloro-4-(2,4-dichlorobenzylaminocarbonyl)-6-[4-(3-chloro)pyridyl]-pyridazine

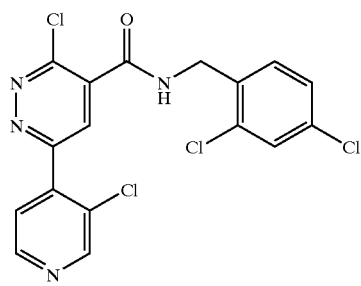

The title compound was prepared by reacting the dichloride (6) with 2,4-dichlorobenzylamine according to Scheme I. Anal. Calcd. for $C_{17}H_{10}Cl_4N_4O$: C, 47.7; H, 2.35; N, 13.09. Found: C, 47.61; H, 2.25; N, 13.06.

EXAMPLE 15

3-Chloro-4-carboxamido-6-[4-(p-toluenesulfonamido)phenyl]pyridazine

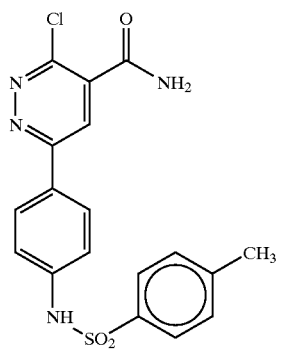

The title compound was prepared via catalytic hydrogenation of the p-nitrophenyl analog (5) of pyridazine followed by toluenesulfonylation and steps 4–5 according to Scheme I. DCI-MS m/z 402 (M+), 403 (mM+H).

EXAMPLE 16

3-Chloro-4-carboxamido-6-(4-quinolyl)pyridazine

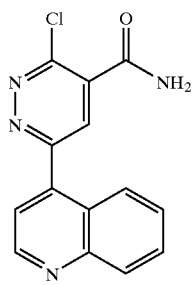

The title compound was prepared from 4-acetylquinoline. $^1$H NMR (MeOD) δ 4.65 (s, 3H), 7.45 (m, 2H), δ 8.80 (d, J=6 Hz, 2H), 7.64 (m, 1H), 7.85 (d, J=8.5 Hz, 1H), 7.93 (d, J=8.8 Hz, 1H), 7.96 (s, 1H), 8.79 (d, J=4.45 Hz, 1H). The intermediate 4-acetylquinoline was prepared by treatment of commercially available 4-quinolinecarboxaldehyde with methylmagnesium chloride in ether followed by oxidation of the resulting secondary alcohol with manganese dioxide.

EXAMPLE 17

3-Chloro-4-carboxamido-6-(phenyl)pyridazine

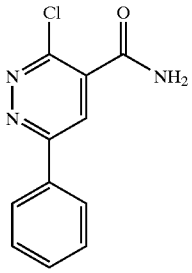

A solution of acetophenone in THF at −70° C. was treated with a solution of lithium diisopropylamide in THF (Scheme II). After 15 min diethyl ketomalonate was added and the reaction was allowed to warm to room temperature. The resulting condensation product 2 (Scheme II) was used following the procedure of Scheme I. DCI-MS m/z 233 (M+), 234 (M+H).

EXAMPLE 18

3-Chloro-4-carboxamido-6-(4-methoxyphenyl)pyridazine

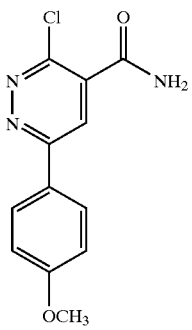

The title compound was prepared from p-methoxyacetophenone in a manner analogous to Example 17. DCI-MS m/z 263 (M+), 264 (M+H).

EXAMPLE 19

3-Chloro-4-carboxamido-6-[3,5-difluoro-4(methylsulfonyl))phenyl]pyridazine

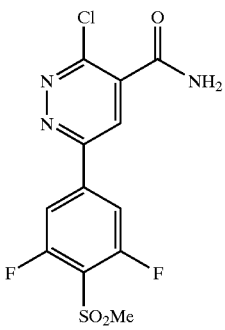

The title compound was prepared from 3,5-difluoro-4-(methylsulfonyl)-acetophenone according to Scheme I. Anal. Calcd. for $C_{12}H_8ClF_2N_3O_3$: C, 41.45; H, 2.32; N, 12.08. Found: C, 41.19; H, 32.26; N. 12.03.

The intermediate 3,5-difluoro-4-(methylsulfonyl)acetophenone was prepared from commercially available 2,6-difluoroaniline according to Scheme III.

EXAMPLE 20

3-Chloro-4-carboxamido-6-[3-fluoro-4(methylsulfonyl)-5-(methoxy)-phenyl]-pyridazine

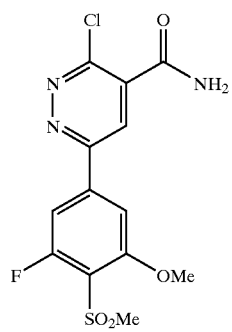

The title compound was prepared by refluxing 3-chloro-4-carboxamido-6-[3,5-difluoro-4(methylsulfonyl)phenyl]pyridazine made in Example 19 in methanol. DCI-MS m/z 359 (M+), 360 (M+H).

EXAMPLE 21

3-Chloro-4-[(phenylalanylcarbamido)-carbonyl]-6-(4-chlorophenyl)pyridazine

The title compound was prepared by treating the dichloride (6) with phenylalanine amide according to Scheme I. DCI-MS m/z 414 (M+), 415 (M+H).

EXAMPLE 22

3-Chloro-4-carboxamido-6-(3-chloro-4-fluorophenyl)pyridazine

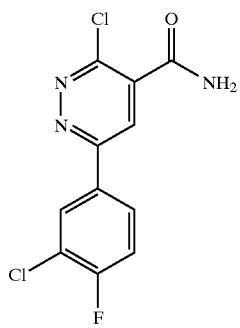

The title compound was prepared from 3-chloro-4-fluoro-acetophenone. DCI-MS m/z 286 (M+H+).

Compounds of the present invention were tested for IL-1β protease inhibition activity according to the following protocol:

Partially purified IL-1β protease is stored at −80° C. thawed on ice, and preincubated for 10 minutes at 37° C. with 2.5 mM dithiothreitol in a buffer solution containing 10 mM Tris-HCl (pH 8.0) and 25% (v/v) glycerol. Inhibitors are prepared as stock solutions in dimethyl sulfoxide (DMSO). The protease is preincubated with inhibitor in a volume of 20 μL in a 1.5 mL polypropylene microcentrifuge tube for 15 minutes at 37° C. The volume of compound added to the assay is adjusted to yield a DMSO concentration in the preincubation of <15% (v/v). The enzyme assay is then initiated by the addition of substrate (TRITC-AYVH-DAPVRS-NH2) to yield a final concentration of 67 μM in a final volume of 30 μL. The reactions are carried out for 60 minutes at 37° C. in the dark and are terminated by the addition of 10 μL of 10% trifluoroacetic acid (TFA). Following the addition of 115 μL of 0.1% TFA, the samples are analyzed by high pressure liquid chromatography using a reverse phase (C18) column and elution with an acetonitrile/water/TFA gradient. Substrate and product are monitored by their absorbance at 550 nm and elute at 4.2 and 5.2 minutes, respectively.

The IL-1β protease inhibitory activity (IC50) for the pyridazine was <100 μM.

Although the invention has been described in the context of particular embodiments, it is intended that the scope of coverage of the patent not be limited to those particular embodiments, but be determined by reference to the following claims.

What is claimed is:

1. A compound of the formula (I) or a pharmaceutically acceptable salt thereof:

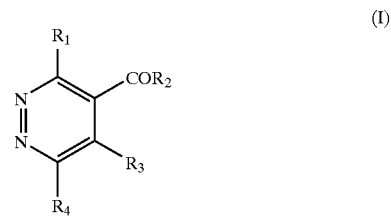

(I)

wherein
$R_1$ is halogen, alkyl sulfonate, aryl sulfonate, alkyl phosphonate, aryl phosphonate, alkyl phosphate or aryl phosphate;
$R_2$ is $OR_5$, $NH(CHR_5)_m$—$COOR_5$, $N(R_5)R_6$ or $NH(CHR_5)_mOH$;
$R_3$ is H or alkyl;
$R_4$ is H, aryl, heteroaryl or alkyl,
wherein said $R_4$ aryl is selected from the group consisting of substituted naphthyl, unsubstituted naphthyl, and substituted phenyl, and
wherein the substituents of said $R_4$ substituted phenyl are selected from the group consisting of halo, lower alkyl, nitro, amino, acylamino, hydroxy, lower alkoxy, alkyl sulfonyl, trifluoromethyl, morpholinoethoxy, morpholinosulfonyl and carbobenzoxy-methyl sulfonyl;
$R_5$ and $R_6$ are independently H, lower alkyl, aryl, hydroxy alkyl, amino alkyl, heteroaryl, lower alkylene-aryl, lower alkylene-heteroaryl or lower cycloalkyl;

m is 0–6; and provided that when $R_1$ is chloro, $R_3$ is H and $R_2$ is $NH_2$, $R_4$ is not 3- or 4-pyridyl.

2. The compound of claim 1 wherein said $R_1$ aryl, $R_5$ aryl and $R_6$ aryl are independently phenyl, naphthyl or substituted phenyl.

3. The compound of claim 2 wherein said phenyl is substituted by halo, lower alkyl, nitro, amino, acylamino, hydroxyl, lower alkoxy, trifluoromethyl, alkyl sulfonyl, morpholinoethoxy or morpholino-sulfonyl.

4. The compound of claim 1 wherein said heteroaryl is pyridyl, thienyl, furyl, thiozolyl, imidazolyl, pyrazolyl, triazinyl, quinolyl or isoquinolyl.

5. A pharmaceutical composition for inhibiting interleukin-1β protease comprising the formula (I) or a pharmaceutically acceptable salt thereof:

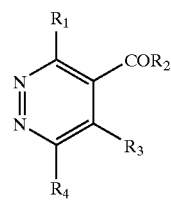

(I)

wherein $R_1$ is halogen, aromatic ether, alkyl sulfonate, aryl sulfonate, alkyl phosphonate, aryl phosphonate, alkyl phosphate or aryl phosphate;

$R_2$ is $OR_5$, $NH(CHR_5)_m$—$COOR_5$, or $NH(CHR_5)_m OH$;

$R_3$ is H or alkyl;

$R_4$ is H, substituted or unsubstituted aryl, heteroaryl or alkyl;

$R_5$ and $R_6$ are independently H, lower alkyl, aryl, hydroxy alkyl, amino alkyl, heteroaryl, lower alkylene-aryl, lower alkylene-heteroaryl or lower cycloalkyl; and m is 0–6 in a pharmaceutically acceptable carrier.

6. A pharmaceutical composition comprising the compound of any one of claims 1–4 or a pharmaceutically acceptable salt thereof.

7. The pharmaceutical composition of claim 6, wherein said composition is useful for inhibiting interleukin-1β protease.

8. A method of inhibiting interleukin-1β protease activity in a mammal in need of such treatment comprising administering to said mammal an effective inhibitory amount of a pharmaceutical composition comprising a compound of the formula (I) or a pharmaceutically acceptable salt thereof:

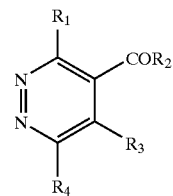

(I)

wherein $R_1$ is halogen, aromatic ether, alkyl sulfonate, aryl sulfonate, alkyl phosphonate, aryl phosphonate, alkyl phosphate or aryl phosphate;

$R_2$ is $OR_5$, $NH(CHR_5)_m$—$COOR_5$, $N(R_5)R_6$ or $NH(CHR_5)_m OH$;

$R_3$ is H or alkyl;

$R_4$ is H, substituted or unsubstituted aryl, heteroaryl or alkyl;

$R_5$ and $R_6$ are independently H, lower alkyl, aryl, hydroxy alkyl, amino alkyl, heteroaryl, lower alkylene-aryl, lower alkylene-heteroaryl or lower cycloalkyl; and m is 0–6 in a pharmaceutically acceptable carrier.

9. A method of treatment of a disease or disorder in a mammal comprising:

administering to said mammal the pharmaceutical composition of claim 6, wherein the disease or disorder is rheumatoid arthritis.

* * * * *